United States Patent [19]

Seemüller et al.

[11] Patent Number: 4,636,489
[45] Date of Patent: Jan. 13, 1987

[54] MODIFIED PROTEASE INHIBITORS, PROCESS FOR THEIR PREPARATION, AND PHARMACEUTICAL COMPOSITIONS PREPARED THEREFROM

[75] Inventors: Ursula Seemüller; Johannes Dodt, both of Munich; Hans Fritz, Hohenbrunn, all of Fed. Rep. of Germany

[73] Assignees: Plantorganwerk KG, Bad Zwischenahn, Fed. Rep. of Germany; Ciba-Geigy Corporation, Ardsley, N.Y.

[21] Appl. No.: 628,355

[22] Filed: Jul. 6, 1984

[30] Foreign Application Priority Data

Jul. 7, 1983 [DE] Fed. Rep. of Germany ....... 3324534

[51] Int. Cl.$^4$ .................. A61K 37/64; C07K 7/10
[52] U.S. Cl. ........................................ 514/12; 530/324
[58] Field of Search ................ 260/112.5 R; 514/12; 530/324

[56] References Cited

U.S. PATENT DOCUMENTS 4,250,086  2/1981  Heavner ................. 260/112.5 R

FOREIGN PATENT DOCUMENTS 2808396  9/1979  Fed. Rep. of Germany .

OTHER PUBLICATIONS

Chem. Abstr. vol. 98, (1983) 121873u.
Chem. Abstr. vol. 97, (1982) 158963d.
Chem. Abstr. vol. 97, (1982) 51668j.
Chem. Abstr. vol. 97, (1982) 51643x.
Chem. Abstr. vol. 87, (1977) 179755w.
Chem. Abstr. vol. 91, (1979) 188735z.
Chem. Abstr. vol. 94, (1981) 152526e.
Chem. Abstr. vol. 94, (1981) 116664q.
Chem. Abstr. vol. 99, (1983) 2569k.
Chem. Abstr. vol. 99, (1983) 2606v.
Klaus Lübke et al., Chemie und Biochemie der Aminosäuren, Peptide und Proteine I, p. 241, and Translation.
Jui-Yoa Chang et al., Methods Enzymol 1983, 91, (Enzyme Structure Part I), pp. 41-48.
R. Knecht et al., Analytical Biochemistry 130, 65-71, (1983).
Molecular Endocrinology, New York, (1977), pp. 27-29, 32 I. MacIntyre Ed.

*Primary Examiner*—Delbert R. Phillips
*Attorney, Agent, or Firm*—Michael W. Glynn; Irving M. Fishman

[57] ABSTRACT

The invention relates to novel, modified eglins B and C, to the preparation thereof, and to pharmaceutical compositions which contain these compounds. Compared with eglin B and C, the modification consists in a terminal shortening. The compounds of the invention can be prepared e.g. by limited enzymatic proteolysis of elgins or by peptide synthesis.

14 Claims, No Drawings

MODIFIED PROTEASE INHIBITORS, PROCESS FOR THEIR PREPARATION, AND PHARMACEUTICAL COMPOSITIONS PREPARED THEREFROM

The present invention relates to novel modified protease inhibitors with the primary structure of eglin B and eglin C, to processes for their preparation, and to pharmaceutical compositions prepared therefrom.

It is known that leech extracts contain protease inhibitors. Two protease inhibitors, designated by the scientific names eglin B and eglin C, are described in DE-OS No. 28 08 396. These substances strongly inhibit chymotrypsin, subtilisin, PMN-granulocyte elastase and cathepsin G, but are only poor inhibitors of trypsin and pancreaselastase. Both eglins consist of 70 amino acid radicals. Their N-terminals (Thr) are identical and they have identical C-terminal sequences (-Val-Gly).

The eglins rank at the present time among the most effective inhibitors of PMN-granulocyte elastase. PMN-granulocyte elastase, a neutral protease, participates in the degeneration of tissues and soluble proteins. Unchecked release of this protease, or these proteases, in the organism can aggravate an inflammatory process and cause tissue degeneration through unspecific proteolysis. Owing to their hitherto known properties the eglins are therefore of great interest for use in medicinal therapy (counteracting inflammation, septic shock, pulmonary emphysema, mucoviscodosis etc.).

It is the object of the present invention to provide modified protease inhibitors, based on eglin B and C, which have a simplified structure and an activity similar to the natural, unmodified products.

Subject of the invention are modified protease inhibitors with the primary structure of eglin B and C, the primary structure of which modified inhibitors is shortened by 2 to 10 amino acid units at the N-terminal of the molecule and/or by 2 to 6 amino acid units at the C-terminal of the molecule.

In particular, the primary structure of modified protease inhibitors with the primary structure of eglin B and eglin C is shortened by 2 to 6 amino acid units at the N-terminal of the molecule and/or by 2 amino acid units at the C-terminal of the molecule.

The primary structure of valuable modified protease inhibitors with the primary structure of eglin C is shortened by 4 to 6 amino acid units at the N-terminal of the molecule and/or by 2 amino acid units at the C-terminal of the molecule.

The modified protease inhibitors of this invention are preferably the modified protease inhibitor F 1 which has the following primary structure:

H-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-H s-Val-Gly-OH and a dissociation constant $K_i = 5.52 \times 10^{-11}$ mole/l for a chymotrypsin complex (substrate: SucAlaAlaProPhepNA), and the modified protease inhibitor F 2 which has the following primary structure:

H-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-G y-OH and a dissociation constant $K_i = 5.37 \times 10^{-11}$ mole/l for a chymotrypsin complex (substrate: SucAlaAlaProPhepNA).

The modified inhibitors of the present invention form complex compounds with chymotrypsin, i.e. they inhibit the protease chymotrypsin. As is evident from Table 1, the dissociation constants of complex compounds of compounds of the present invention are comparable to those of eglin C.

TABLE 1

| | $K_i$ (mole/l) | protease inhibited |
|---|---|---|
| eglin C | $8 \times 10^{-10}$ (a) | leucocyte elastase |
| | $5 \times 10^{-11}$ | leucocyte cathepsin G |
| modification product F 1 | $5.52 \times 10^{-11}$ (b) | chymotrypsin |
| modification product F 2 | $5.37 \times 10^{-11}$ (b) | chymotrypsin |

(a) substrate: SucAlaAlaProValNMec,
(b) substrate: SucAlaAlaProPhepNA

The dissociation constants are determined by the known method of N. M. Green and E. Work, which is described in the Biochemical Journal 54, pp. 347–352.

The shortened eglines of the present invention are modified products the inhibitory effect of which is, surprisingly, fully retained.

The protease inhibitors of this invention are distinguished by a number of advantages. Because of their shortened peptide chain as compared with the eglins, they are more easily synthesised and, in addition, they are less allergenic in activity and have a better absorptive capacity.

The compounds of this invention can be obtained e.g. by enzymatic degradation of eglin B or C or by chemical synthesis.

Enzymatic degradation of eglin B or C according to this invention is effected by a limited proteolysis using peptidases such as carboxypeptidases, i.e. proteases which cleave an amino acid chain from the carboxyl end, and aminopeptidases, i.e. proteases which attack an amino acid chain from the amino end. Proteases which are suitable for the process of this invention and which may be attached to carriers are carboxypeptidase A, leucineaminopeptidase and cathepsins A, B, C and D. However, carboxypeptidase Y and cathepsin C are particularly suitable. Cathepsin C, as dipeptidylaminopeptidase, splits off dipeptides sequentially from the unsubstituted amino end of proteins. The mode of action of cathepsin may be seen from the following comparison of amino acid sequences (beginning at the N-terminal) of eglin C, and the modification products F 1 and F 2 obtainable by degradation with cathepsin C.

eglin C:
    Thr Glu Phe Gly Ser Glu Leu Lys Ser Phe Pro Glu Val Val . . .
F 1:                      Ser Glu Leu Lys Ser Phe Pro Glu Val Val . . .
F 2:                                Leu Lys Ser Phe Pro Glu Val Val . . .

Said process for the preparation of modified protease inhibitors by limited proteolysis comprises (a) putting eglin B or C into a suitable buffer system of pH 4 to 7, (b) adding a peptidase, dissolved in a suitable buffer system, and, if desired, 0.5% of sodium lauryl sulfate, (c) incubating the mixture for 2 to 72 hours at 10° to 40° C.,
(d) purifying the reaction mixture by chromatography, and
(e) desalting.

The process for the preparation of modified inhibitor F 1 preferably comprises
(a) dissolving eglin C in 1% acetic acid,
(b) adding to the above solution a solution of cathepsin C (20 U/1.14 ml) in a buffer system consisting of 4% pyridine, water, 0.5% acetic acid, 0.1N HCl, 0.375M 2-mercaptoethanol, 0.2 M EDTA, and adjusting the pH to 5.0,
(c) incubating the batch for 4 hours at 37° C., and
(d) purifying the reaction mixture on a Sephadex SP-C25 cation exchanger by equilibrating with 0.05M ammonium acetate of pH 5.0 and eluting with a gradient of pH 5.0, prepared from equal parts by volume of 0.05M ammonium acetate and 0.4M sodium chloride in 0.05M ammonium acetate.

The process for the preparation of the modified inhibitor F 2 comprises
(a) dissolving eglin C in 1% acetic acid,
(b) adding to the above solution a solution of cathepsin C (20 U/1.14 ml) in a buffer system consisting of 4% pyridine, water, 0.5% acetic acid, 0.1N hydrochloric acid, 0.375M 2-mercaptoethanol, 0.2M EDTA, and adjusting the pH to 5.0,
(c) incubating the batch for 48 hours at 37° C., and
(d) purifying the reaction mixture on a Sephadex SP-C25 cation exchanger by equilibrating with 0.05M ammonium acetate of pH 5.0 and eluting with a gradient of pH 5.0, prepared from equal parts by volume of 0.05M ammonium acetate and 0.4M sodium chloride in 0.05M ammonium acetate, but eluting first the modified protease inhibitor F 1, then the modified protease inhibitor F 2.

It will be readily understood that the incubation time determines the degree of degradation of the eglin molecule. For example, when degrading eglin C with cathepsin C, modification product F 1 only is obtained after an incubation of 4 hours, modification product F 1 together with modification product F 2 after 24 hours, and preponderantly modification product F 2 after 48 hours. The reaction course can be followed with the aid of disc electrophoresis (pH 8.9; 15% gel; corresponding to a No. 2 Maurer system). The $R_f$ values obtained are:
eglin C: 0.52
modification product F 1: 0.42
modification product F 2: 0.3.

The modified inhibitors F 1 and F 2 obtained as mentioned above are electrophoretically homogeneous (confirmation by discontinuous gel electrophoresis in a No. 2 Maurer gel system).

Further, the compounds of this invention can be obtained by chemical means. A chemical synthesis can be carried out using corresponding amino acid units, which may be suitably protected, and in a manner which is known per se. In particular, such a peptide synthesis comprises removing any protecting groups present in a compound corresponding to the compounds of the invention in which at least one of those amino, hydroxyl and/or carboxyl groups present carries a protecting group. Such a synthesis is illustrated in more detail by the following scheme which exemplifies the synthesis of the modified protease inhibitors F 1 and F 2 (abbreviations according to Houben-Weyl, Vol. 15/1; Synthese von Peptiden, Georg Thieme Verlag, Stuttgart, 1974):

1. Synthesis of modified protease inhibitor F 1

| 1 | 2 | 3 | 4 | 5 | 6 | 7 | 8 | 9 | 10 |
|---|---|---|---|---|---|---|---|---|---|
| H—Ser—|Glu—|Leu—|Lys—|Ser—|Phe—|Pro—|Glu—|Val—|Val— |

| 11 | 12 | 13 | 14 | 15 | 16 | 17 | 18 | 19 | 20 |
|---|---|---|---|---|---|---|---|---|---|
| —Gly—|Lys—|Thr—|Val—|Asp—|Gln—|Ala—|Arg—|Glu—|Tyr— |

| 21 | 22 | 23 | 24 | 25 | 26 | 27 | 28 | 29 | 30 |
|---|---|---|---|---|---|---|---|---|---|
| —Phe—|Thr—|Leu—|His—|Tyr—|Pro—|Gln—|Tyr—|Asp—|Val— |

| 31 | 32 | 33 | 34 | 35 | 36 | 37 | 38 | 39 | 40 |
|---|---|---|---|---|---|---|---|---|---|
| —Tyr—|Phe—|Leu—|Pro—|Glu—|Gly—|Ser—|Pro—|Val—|Thr— |

| 41 | 42 | 43 | 44 | 45 | 46 | 47 | 48 | 49 | 50 |
|---|---|---|---|---|---|---|---|---|---|
| —Leu—|Asp—|Leu—|Arg—|Tyr—|Asn—|Arg—|Val—|Arg—|Val— |

| 51 | 52 | 53 | 54 | 55 | 56 | 57 | 58 | 59 | 60 |
|---|---|---|---|---|---|---|---|---|---|
| —Phe—|Tyr—|Asn—|Pro—|Gly—|Thr—|Asn—|Val—|Val—|Asn— |

| 61 | 62 | 63 | 64 | 65 | 66 |
|---|---|---|---|---|---|
| —His—|Val—|Pro—|His—|Val—|Gly—OH |

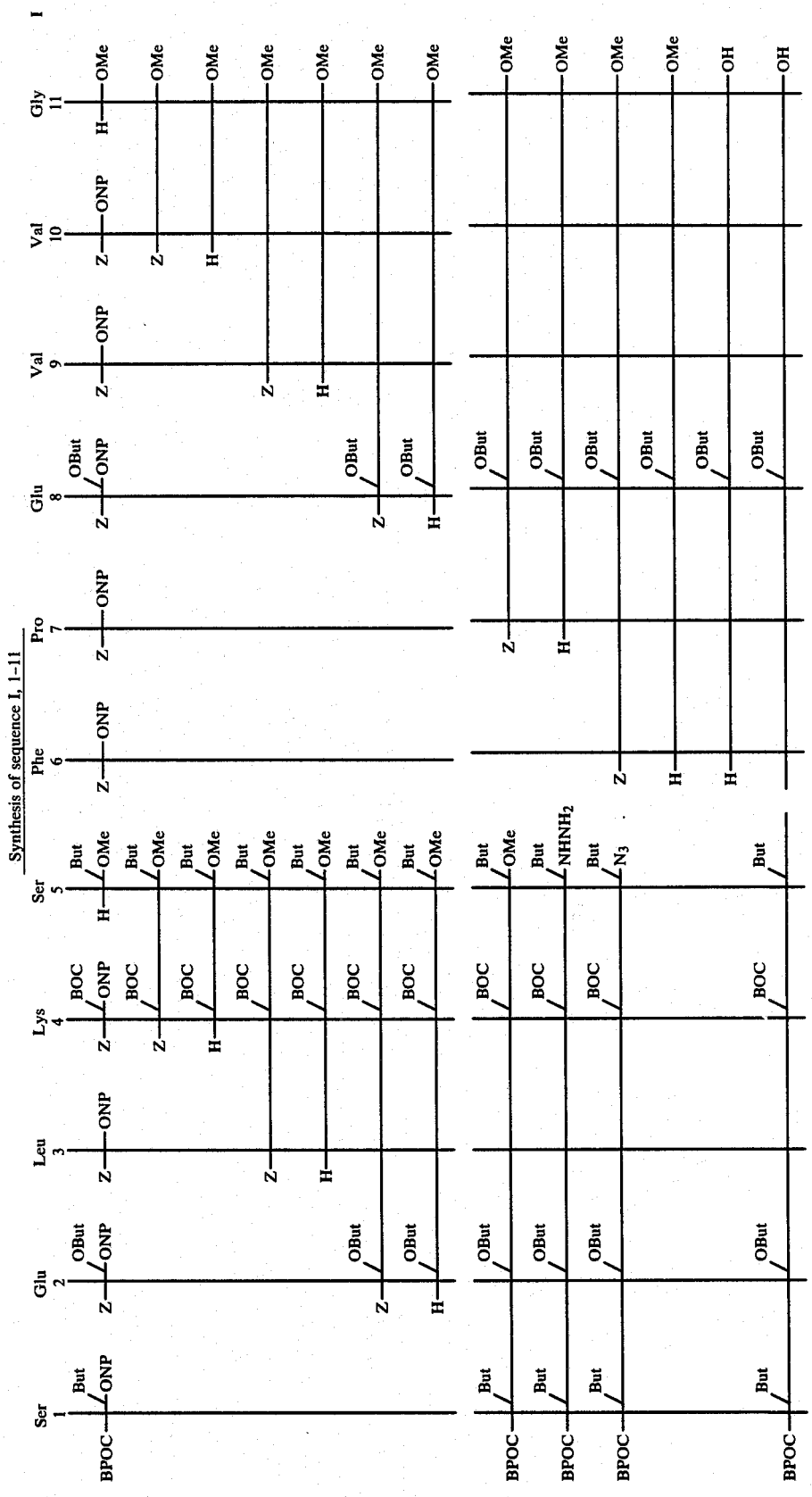

Synthesis of sequence II, 12-21 (Arg[18] protected by protonation)
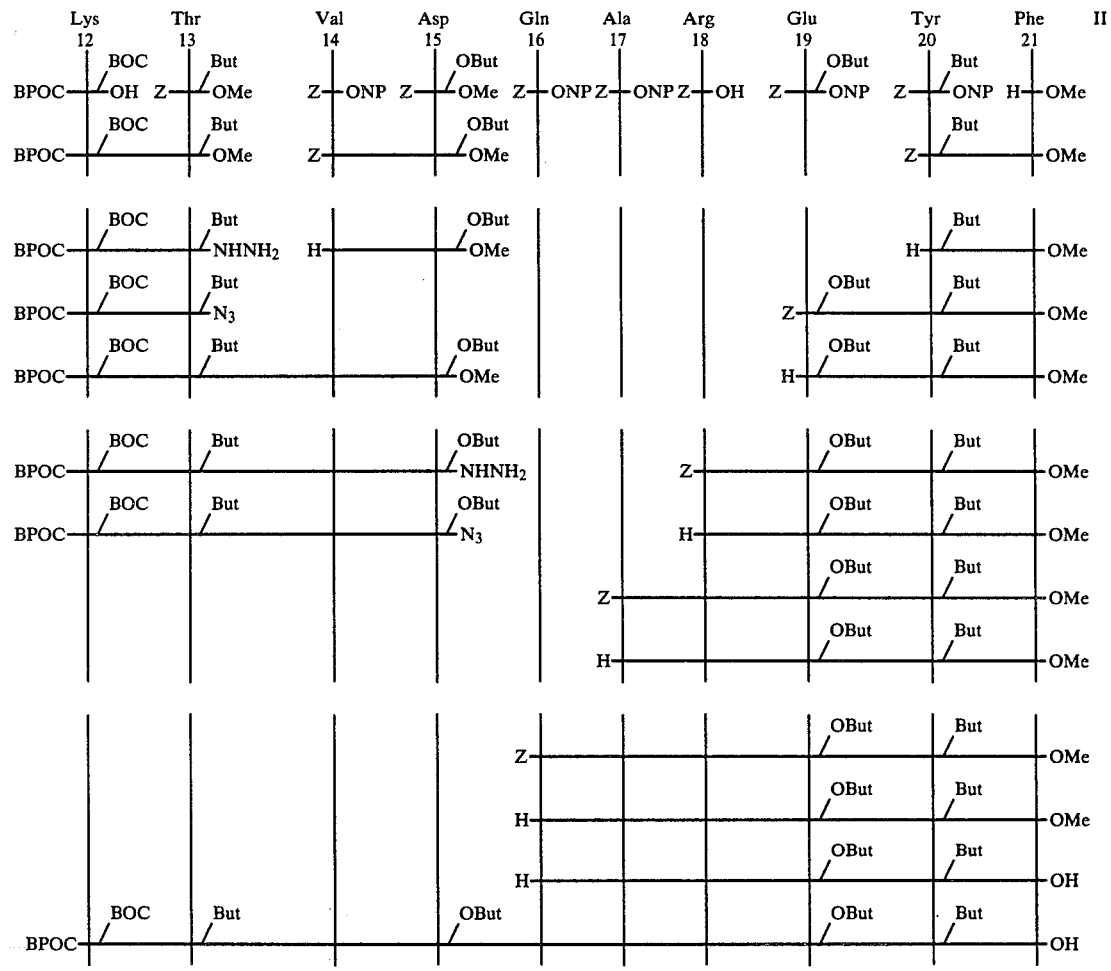
Synthesis of sequence III, 22-29 (His[24] not protected)
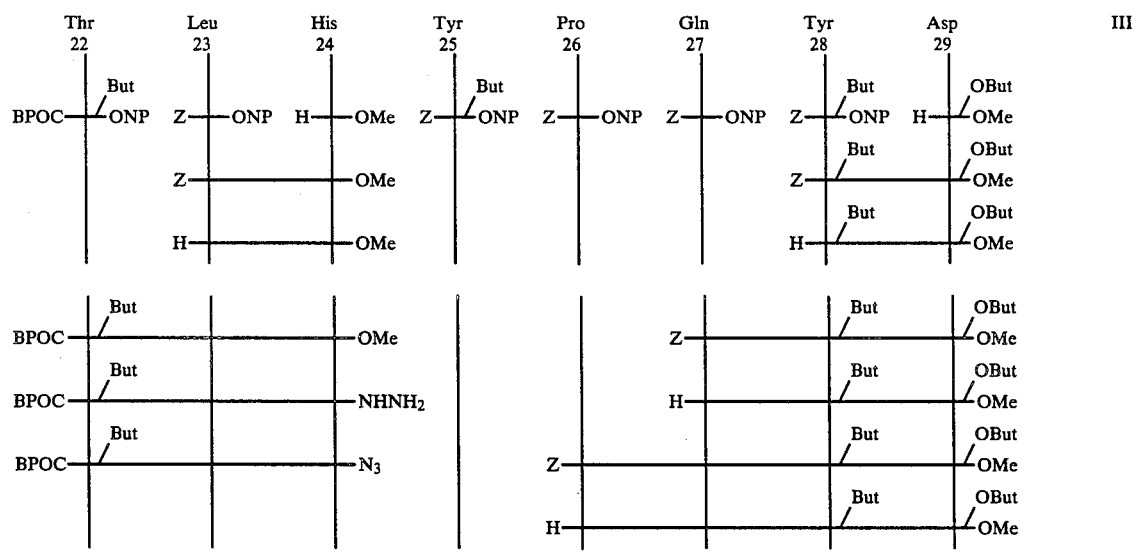

-continued
Synthesis of sequence III, 22–29 (His[24] not protected)
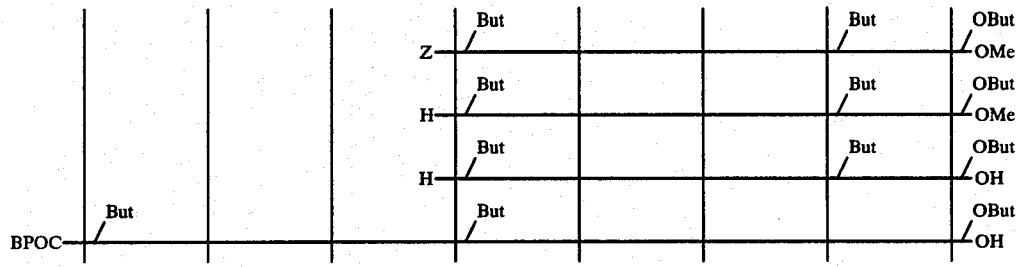
Synthesis of sequence IV, 30–36
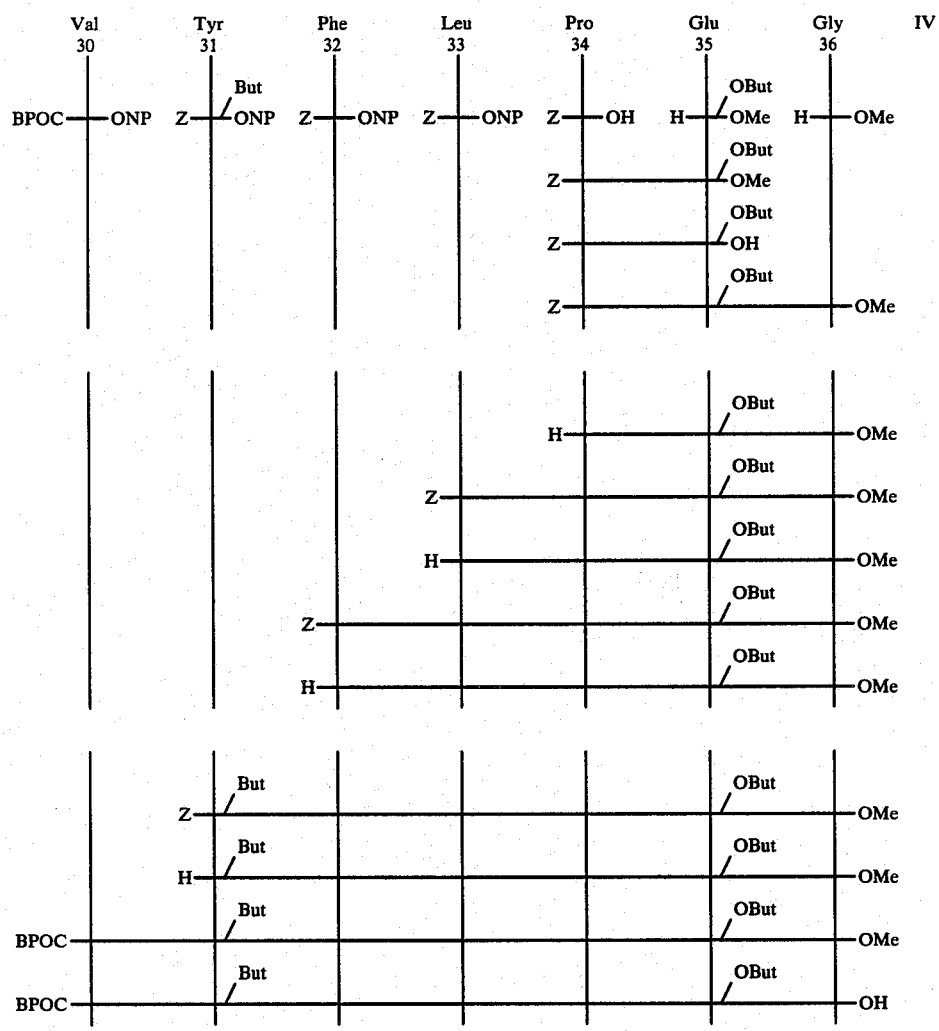
Synthesis of sequence V, 37–45 (Arg[44] protected by protonation)

Synthesis of sequence V, 37–45 (Arg$^{44}$ protected by protonation)
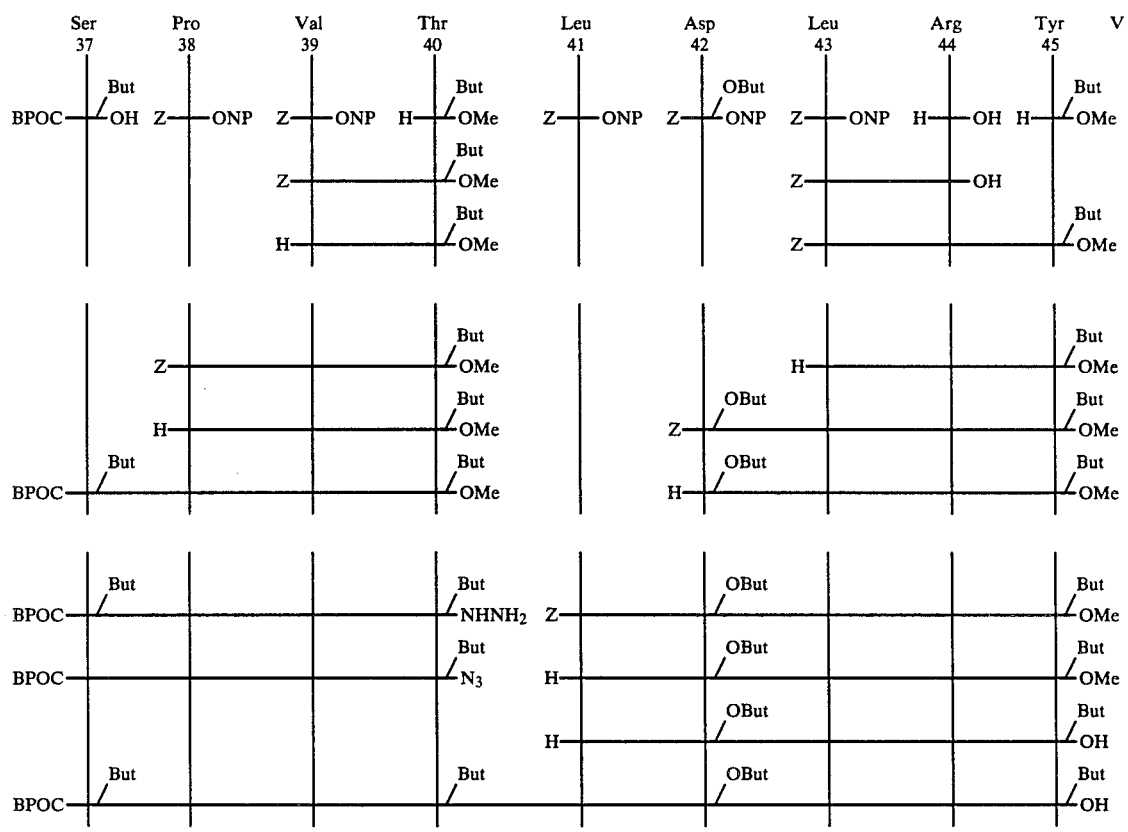
Synthesis of sequence VI, 46–55 (Arg$^{47,49}$ protected by protonation)
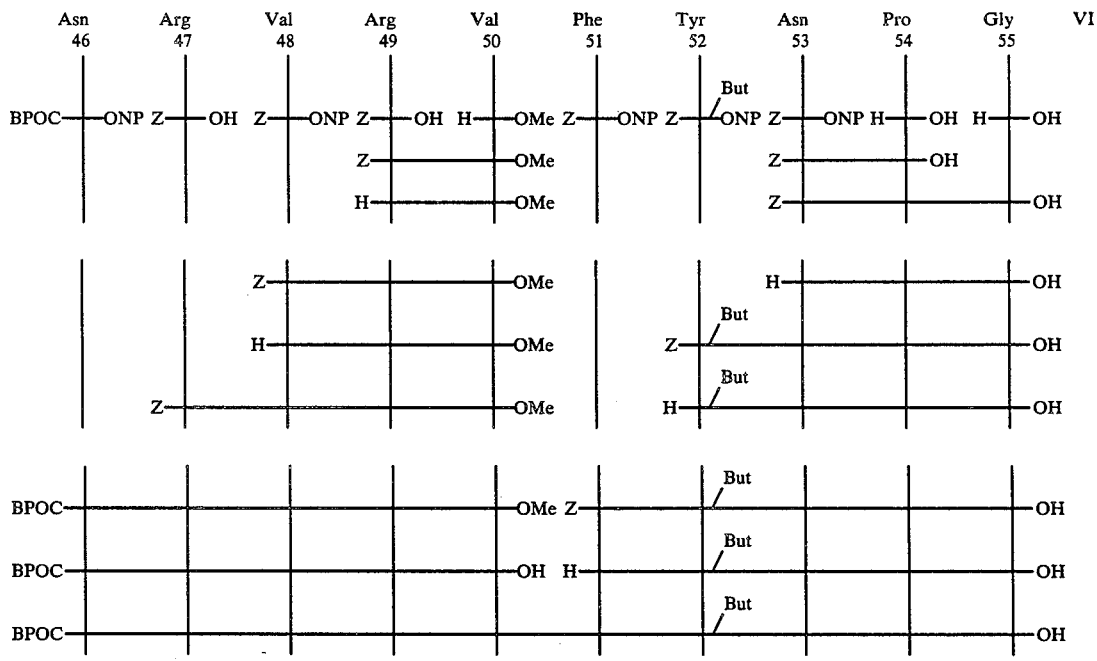

Synthesis of sequence VII, 56-66 (His[61,64] not protected)

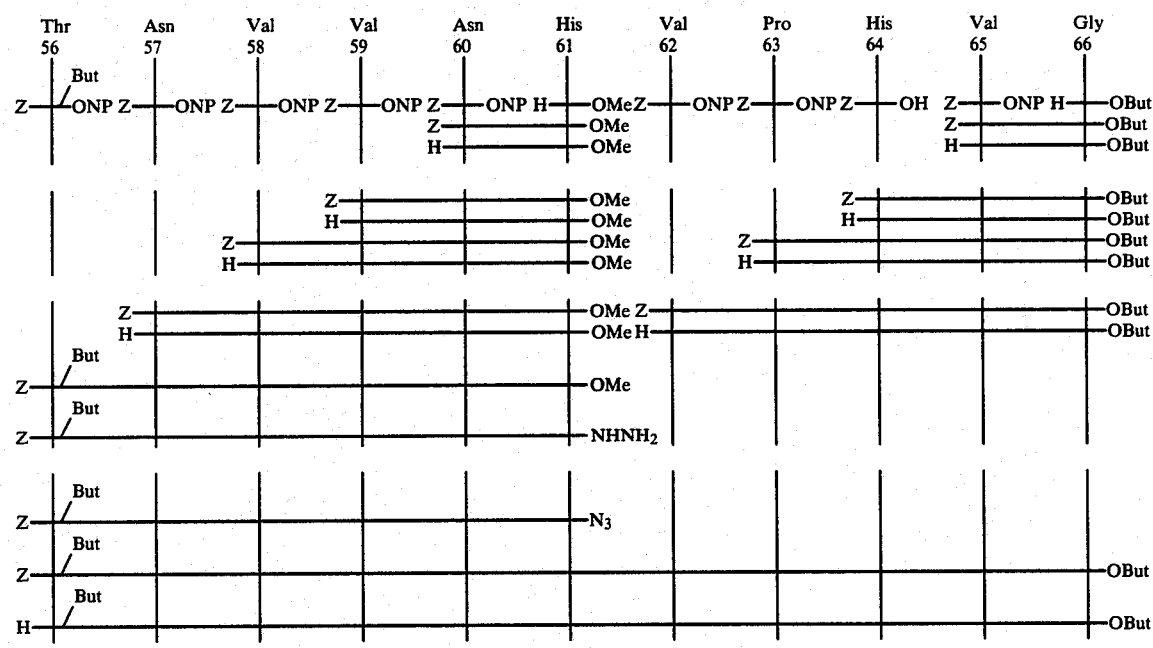

Synthesis of protected and deprotected sequence 1-66 using partial sequences described hereinbefore

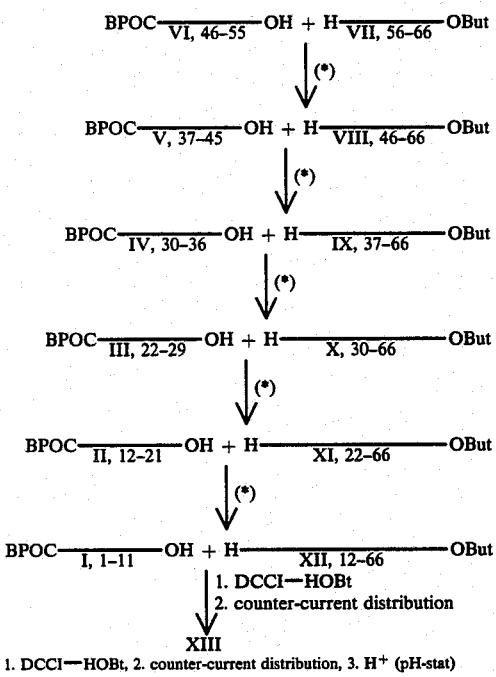

(*) 1. DCCI—HOBt, 2. counter-current distribution, 3. H+ (pH-stat)

2. Synthesis of modified protease inhibitor F 2

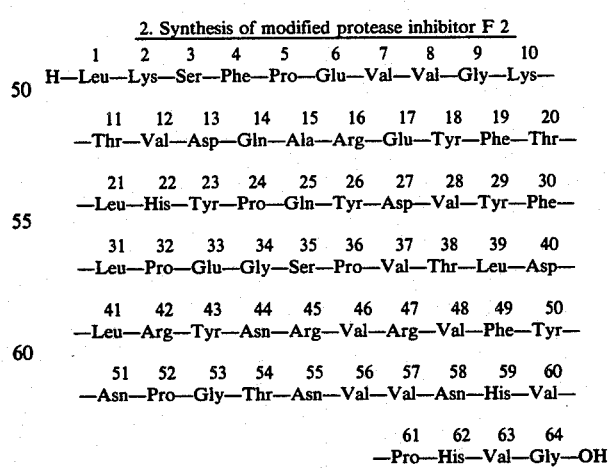

This compound is synthesised by using the above synthesised sequence XII and coupling wih the protected nonapeptide XV described below.

Synthesis of nonapeptide XV, 1-9, used for the preparation of inhibitor F 2

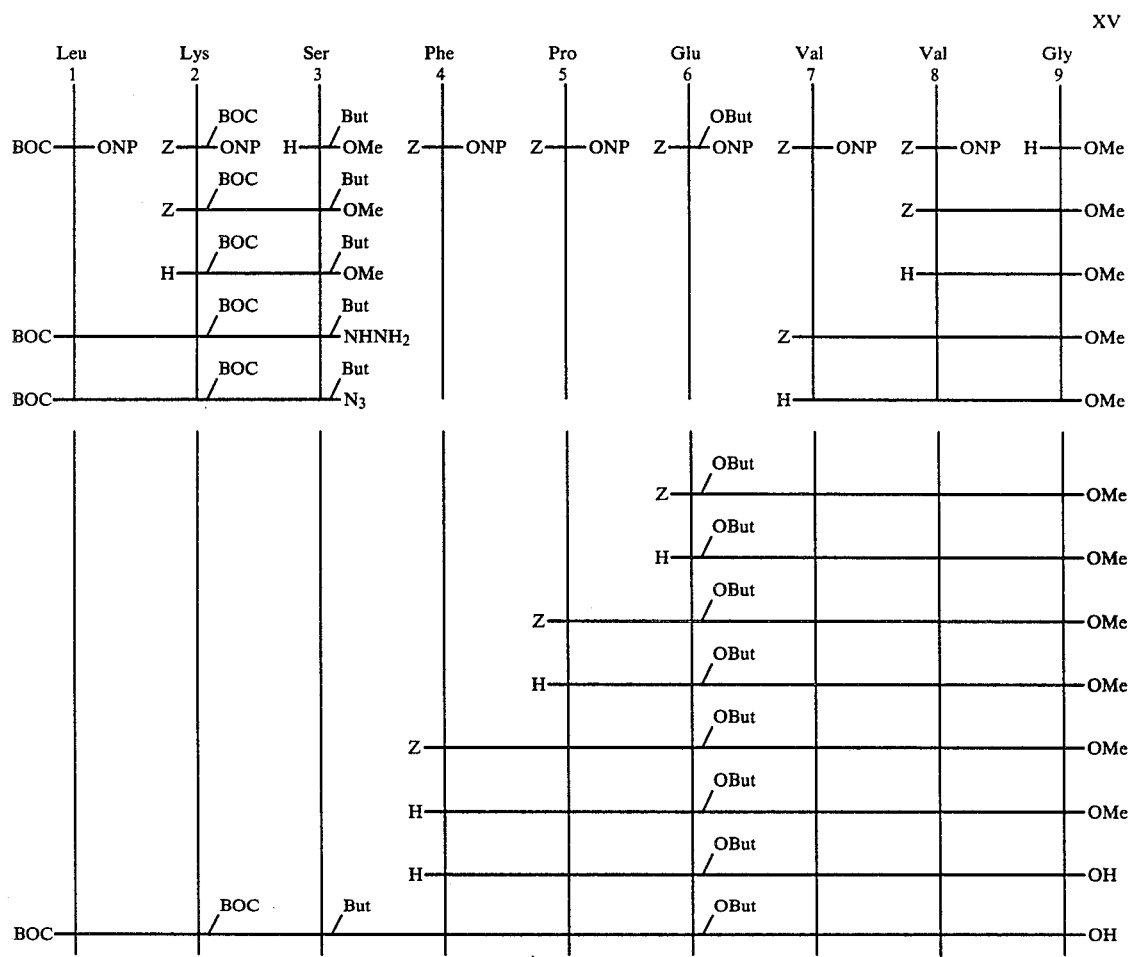

The procedure is continued as follows:

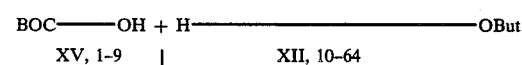

```
                    XV, 1-9              XII, 10-64
```

The enumeration of the 55 amino acid units of sequence XII is altered as compared with that of F 1, as the complete modified inhibitor F 2 has two amino acids less

↓

XVI

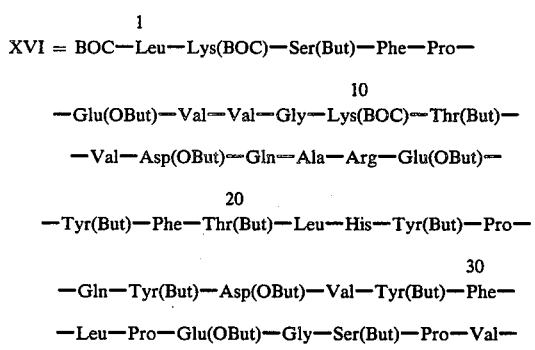

-continued

—Thr(But)—Leu—Asp(OBut)—Leu—Arg—Tyr(But)—

—Asn—Arg—Val—Arg—Val—Phe—Tyr(But)—Asn—

—Pro—Gly—Thr(But)—Asn—Val—Val—Asn—His—

—Val—Pro—His—Val—Gly—OBut 1. 90% Trifluoroacetic acid
2. Ion exchanger Trifluoroacetate versus acetate
3. counter-current distribution

↓

XIV = modified inhibitor F 2

The modified eglins obtainable according to this invention have valuable pharmacological properties and, like the eglins (q.v. for example DE-OS No. 2 808 396), can be used prophylactically or, in particular, therapeutically.

Thus the novel compounds of this invention can be used for the prophylactic and therapeutic treatment of pulmonary diseases, e.g. those caused by leucocyte elastase, such as pulmonary emphysema and ARDS (acute respiratory distress syndrome), and also, if necessary, mucoviscidosis, as well as septic shock. In addition, they can be used as anti-inflammatory agents. Accordingly, the present invention also relates to the use of the novel modified eglin compounds for the prophylactic and therapeutic treatment of the conditions referred to above.

The invention also relates to pharmaceutical compositions which contain at least one of the novel compounds, if desired together with a pharmaceutically acceptable carrier and/or adjuvants. These compositions can be used in particular for the above indications when administered e.g. parenterally (such as intravenous or intrapulmonary administration) or applied topically. The dosage depends in particular on the specific drug formulation and on the object of the therapy or prophylactic treatment.

Administration is made by intravenous injection or by intrapulmonary means, for example by inhalation using a Bird inhalator. Accordingly, pharmaceutical compositions for parenteral administration in single dosage form contain about 10 to 50 mg of active ingredient per dose, depending on the kind of administration. In addition to the active ingredient, the pharmaceutical compositions of the invention will normally contain sodium chloride, mannitol or sorbitol for adjusting the isotonicity of the formulation. They may be in lyophilised form or in the form of solutions. Solutions will conveniently contain an antibacterial preservative, e.g. 0.2 to 0.3% of methyl or ethyl 4-hydroxybenzoate.

A composition for topical application can be in the form of an aqueous solution, a lotion or jelly, an oily solution or suspension, or a fatty ointment or, preferably, an emulsion ointment. A composition in the form of an aqueous solution is obtained, for example, by dissolving the active ingredient in an aqueous buffer solution of pH 4 to 7.5 and, if desired, adding a further active ingredient, e.g. an anti-inflammatory agent, and/or a polymer binder such as polyvinylpyrrolidone, and/or a preservative. The concentration of active ingredient is from about 0.1 to 5 mg, preferably from 0.25 to 1.0 mg, in 10 ml of a solution or 10 g of a jelly.

An oily formulation for topical application is obtained, for example, by suspending the active ingredient in an oil, if desired with the addition of a swelling agent such as aluminium stearate, and/or a surface-active agent (surfactant) whose HLB value (hydrophilic/lipophilic balance) is below 10, for example a fatty acid monoester of a polyalcohol, e.g. glycerol monostearate, sorbitan monolaurate, sorbitan monostearate or sorbitan monooleate. A fatty ointment is obtained, for example, by suspending the active ingredient in a speadable fatty base, if desired with the addition of a surfactant whose HLB value is below 10. An emulsion ointment is obtained by triturating an aqueous solution of the active ingredient in a soft spreadable fatty base, with the addition of a surfactant whose HLB value is below 10. All these topical formulations can also contain a preservative. The concentration of active ingredient is from about 0.1 to 5 mg, preferably from 0.25 to 1.0 mg, in about 10 g of the base.

Inhalation preparations for treatment of the respiratory passages by intrapulmonary administration are, for example, aerosols or sprays which can distribute the pharmacological active ingredient in the form of drops of a solution or suspension. Preparations containing a solution of the active ingredient also contain a suitable propellant and, if necessary, an additional solvent and/or a stabiliser. Instead of a propellant gas, it is also possible to use compressed air, which can be produced as required by a suitable compression and pressure release means.

Particularly suitable devices for administration are Bird inhalators which have been introduced into medicine and are known. These function by putting a solution of the active ingredient into the device, atomising the solution under slight overpressure, and introducing it into the lungs of the patient.

Depending on the age, individual condition and nature of the illness, the dose for a warm-blooded animal (humans and animals) of about 70 kg body weight is from 10 to 30 mg per inhalation by intrapulmonary administration (once or twice daily), and from about 10 to 150 mg daily for intravenous administration, e.g. also by continuous drip infusion.

Therapeutically effective sputum and plasma concentrations, which can be determined by immunological methods such as ELISA, are from about 10 to 200 μg/ml.

The following examples are intended to illustrate the invention and are not to be construed as being limitations thereon.

EXAMPLE 1

Preparation of modified inhibitor F 1 by limited proteolysis

An incubation solution is prepared by adding a solution of cathepsin C (20 U/1.14 ml) to 200 μl of a buffer system consisting of 40 μl of 4% pyridine, 79 μl of water, 40 μl of 0.5% acetic acid, 32 μl of 0.1N hydrochloric acid, 8 μl of 0.375M 2-mercaptoethanol, and 2 μl of 0.2M EDTA. 1 ml of a cathepsin C incubation solution is added to a solution of 2.7 mg of eglin C (337 nmoles) in 150 μl of 1% acetic acid and the batch is adjusted to pH 5.0. After incubation for 4 hours at 37° C., the batch is applied to a Sephadex SP-C25 cation exchanger (column: 0.5 cm×50 cm). The material in the column is equilibrated with 0.05M ammonium acetate of pH 5.0. After 5 hours the column is eluted with a gradient of pH 5.0, prepared from equal parts by volume (250 ml) of 0.05M ammonium acetate and 0.4M sodium chloride in 0.05M ammonium acetate. The rate of flow is adjusted to 1.6 ml/h. The volumes of the fractions are 0.8 ml.

For desalting, the fractions are diafiltered in an Amicon 8 MC micro-ultrafiltration system against 1% acetic acid with a UM2 membrane.

In disc electrophoresis (pH 8.9; 15% gel; corresponding to a No. 2 Maurer system), the modified inhibitor F 1 obtained as above has an $R_f$-value of 0.42 and a dissociation constant $K_i = 5.52 \times 10^{-11}$ mole/l.

For amino acid analyses, desalted aliquots are hydrolysed for 24 and 48 hours under nitrogen in vacuo and analysed in an amino acid analyser (Durrum, 2 nmole programme). N-Terminal determinations are carried out by the dansyl technique. A 10-step Edman degradation is carried out for an unequivocal assignment of the sequences.

EXAMPLE 2

Preparation of modified inhibitor F 2 by limited proteolysis

The procedure for the preparation of the modified inibitor F 2 is the same as that described above, except that the reaction solution is incubated for 48 hours at 37° C. When chromatographing the reaction mixture, the modified inhibitor F 1 is eluted first, and then the modified inhibitor F 2

In disc electrophoresis (pH 8.9; 15% gel; corresponding to a No. 2 Maurer system), the modified inhibitor F 2 has an $R_f$ value of 0.3 and a dissociation constant $K_i = 5.37 \times 10^{-11}$ mole/l.

Amino acid analyses, N-terminal determinations and Edman degradation for assignment of the sequences are carried out as for inhibitor F 1.

EXAMPLE 3

Pharmaceutical composition containing the modified protease inhibitor F 1 or F 2 for parenteral administration A solution prepared according to either Example 1 or 2 is dialysed against a 0.9% NaCl solution. The concentration of the solution is then adjusted to 1 mg/ml or 10 mg/ml by dilution with the same NaCl solution. These solutions are sterilised by ultrafiltration (membranes with 0.22 μm pores).

The sterilised solutions can be used direct for intravenous administration, for continuous drip infusion, and for atomising in an inhalator (e.g. a Bird inhalator).

What is claimed is:

1. A peptide having the primary structure of eglin B or C which is shortened by 2-6 amino acids units at the N-terminus.

2. The peptide of claim 1 which is shortened by 4 or 6 units at the N-terminus.

3. A protease inhibitor F 1 according to claim 1, which has the following primary structure:

H-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-H s-Val-Gly-OH and a dissociation constant of $K_i = 5.52 \times 10^{-11}$ mole/l for a chymotrypsin complex (substrate: SucAlaAlaProPhepNA).

4. A protease inibitor F 2 according to claim 1, which has the following primary structure:

H-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-G y-OH and a dissociation constant $K_i = 5.37 \times 10^{-11}$ mole/l (substrate: SucAlaAlaProPhepNA) for a chymotrypsin complex.

5. A pharmaceutical preparation comprising a protease inhibiting amount of a compound of claim 1 and a pharmaceutically acceptable carrier.

6. A pharmaceutical preparation comprising a protease inhibiting amount of a compound of claim 2 and a pharmaceutically acceptable carrier.

7. A pharmaceutical preparation comprising a protease inhibiting amount of a compound of claim 3 and a pharmaceutically acceptable carrier.

8. A pharmaceutical preparation comprising a protease inhibiting amount of a compound of claim 4 and a pharmaceutically acceptable carrier.

9. A method of treating a disease responsive to eglin B or C in a warm-blooded animal comprising administering to said animal a protease inhibiting amount of a compound of claim 1.

10. A method of treating a protease mediated degenerative disease in a mammal in need of such treatment comprising administering to said mammal a protease inhibiting amount of a compound of claim 1.

11. A method of inhibiting the action of protease comprising applying a protease inhibiting amount of a compound of claim 1 to a protease containing entity so that the enzymatic activity of said protease is inhibited.

12. A method of inhibiting the action of protease comprising applying a protease inhibiting amount of a compound of claim 2 to a protease containing entity so that the enzymatic activity of said protease is inhibited.

13. A method of inhibiting the action of protease comprising applying a protease inhibiting amount of a compound of claim 3 to a protease containing entity so that the enzymatic activity of said protease is inhibited.

14. A method of inhibiting the action of protease comprising applying a protease inhibiting amount of a compound of claim 4 to a protease containing entity so that the enzymatic activity of said protease is inhibited.

* * * * *